United States Patent [19]

Rizkalla

[11] Patent Number: 4,659,518
[45] Date of Patent: * Apr. 21, 1987

[54] PREPARATION OF CARBOXYLIC ACIDS

[75] Inventor: Nabil Rizkalla, River Vale, N.J.

[73] Assignee: The Halcon SD Group, Inc., Little Ferry, N.J.

[*] Notice: The portion of the term of this patent subsequent to Nov. 13, 2001 has been disclaimed.

[21] Appl. No.: 219,786

[22] Filed: Dec. 24, 1980

[51] Int. Cl.⁴ ............................................. C07C 51/12
[52] U.S. Cl. ................................... 260/413; 502/161; 502/162; 502/167; 560/232; 562/406; 562/497; 562/517; 562/519
[58] Field of Search ............... 260/413; 562/519, 517, 562/406, 497; 560/232, 204, 114, 97; 252/429; 502/161, 162, 167

[56] References Cited

U.S. PATENT DOCUMENTS

| 2,650,245 | 8/1953 | Thomas et al. | 562/519 |
| 4,133,963 | 1/1979 | Holmes | 562/519 |
| 4,482,497 | 11/1984 | Rizkalla | 260/413 |

FOREIGN PATENT DOCUMENTS 2749955 5/1978 Fed. Rep. of Germany ...... 562/519

Primary Examiner—Vivian Garner
Attorney, Agent, or Firm—Harold N. Wells

[57] ABSTRACT

A carboxylic acid, such as acetic acid, is prepared by carbonylation of a hydrocarbyl alcohol, such as methanol, by the use of a molybdenum-nickel or tungsten-nickel co-catalyst in the presence of a promoter comprising an organo-phosphorus compound or an organo-nitrogen compound wherein the phosphorus and nitrogen are trivalent and in the presence of an iodide.

2 Claims, No Drawings

PREPARATION OF CARBOXYLIC ACIDS

This invention relates to the preparation of carboxylic acids, more particularly mono-carboxylic acids, and especially lower alkanoic acids, such as acetic acid, by carbonylation.

Acetic acid has been known as an industrial chemical for many years and large amounts are used in the manufacture of various products. Proposals for producing carboxylic acids by the action of carbon monoxide upon alcohols (carbonylation) have been described, for example, in Reppe et al. U.S. Pat. No. 2,729,651 and in Holmes U.S. Pat. Nos. 4,133,963 and 4,218,340. However, such prior proposals involving carbonylation reactions have required the use of very high pressures. Carbonylation processes effective at lower pressures have also been proposed. French Patent No. 1,573,130, for example, describes the carbonylation of methanol and mixtures of methanol with methyl acetate in the presence of compounds of Group VIII noble metals such as iridium, platinum, palladium, osmium and ruthenium and in the presence of bromine or iodine under more moderate pressures than those contemplated by Reppe et al. and Holmes. U.S. Pat. Nos. 3,769,329 and 3,772,380 produce acetic acid from the same reactants using an iridium or rhodium component with bromine or iodine. Schultz (U.S. Pat. Nos. 3,689,533 and 3,717,670) has disclosed a vapor-phase process for acetic acid production employing various catalysts comprising a rhodium component dispersed on a carrier. These lower-pressure carbonylation disclosures, however, require the use of expensive noble metals. More recently, Belgian Patent No. 860,557 has proposed the preparation of carboxylic acids by carbonylation of alcohols in the presence of a nickel catalyst promoted by a trivalent phosphorus compound and in the presence of an iodide. In this process low pressure carbonylation is made possible without the use of a noble metal. This process is effective but there is room for improvement in terms of yields of the desired acid.

It is accordingly an object of the present invention to provide an improved process for the manufacture of carboxylic acids, especially lower alkanoic acids, such as acetic acid, which requires neither high pressures nor Group VIII noble metals and makes possible the production of carboxylic acids in high yields in short reaction times.

In accordance with the invention, carbonylation of a hydrocarbyl alcohol is carried out by using a molybdenum-nickel or a tungsten-nickel co-catalyst in the presence of a promoter comprising an organo-phosphorus compound or an organo-nitrogen compound wherein the phosphorus and nitrogen are trivalent, and in the presence of an iodide. The surprising discovery has been made that this co-catalyst in combination with the promoteriodide system of the character indicated makes possible carbonylation of alcohols not only at relatively low pressures but rapid, high yield production of carboxylic acids.

Thus, in accordance with the invention, carbon monoxide is reacted with a hydrocarbyl alcohol such as a lower alkyl alcohol, to produce a carboxylic acid, such as a lower alkanoic acid, the carbonylation taking place in the presence of an iodide, e.g., a hydrocarbyl iodide, especially a lower alkyl iodide, such as methyl iodide, and in the presence of the co-catalyst and promoter combination which has been identified above. Acetic acid for example, can be effectively prepared in a representative case by subjecting methyl alcohol to carbonylation. While it is preferred to charge the alcohol directly to the reaction, alcohol precursors such as esters, e.g., methyl acetate, or ethers, e.g., dimethyl ether, can be used in combination with equivalent amounts of water. Reference to alcohols, therefore, includes such precursors.

In like manner, other lower alkanoic acids, such as propionic acid, butyric acid, and valeric acid, can be produced by carbonylating the corresponding lower alkyl alcohol such as ethyl alcohol, propyl alcohol, and the like. Similarly, other alkanoic acids, such as those containing up to 12 carbons, for example capric acid, caprylic acid, and lauric acid, and like higher carboxylic acids are produced by carbonylating the corresponding alcohol, e.g., alkyl alcohols containing up to 11 carbon atoms in the alkyl group, heptyl alcohol, nonyl alcohol, undecyl alcohol, phenol, and the like.

The above-described reaction can be expressed as follows:

$$CO + ROH \rightarrow RCOOH \qquad (1)$$

wherein R is a hydrocarbyl radical which may be saturated, e.g., alkyl of
  1 to 11 carbon atoms, or monocyclic aryl, e.g., phenyl or aralkyl, e.g., benzyl. Preferably, R is lower alkyl, i.e., an alkyl group of 1 to 4 carbon atoms, such as methyl, ethyl, n-propyl, i-propyl, n-butyl, sec-butyl, and t-butyl.

The hydrocarbyl radical may be substituted with substituents which are inert in the reactions of the invention.

The more volatile components such as alkyl iodide and unreacted alcohol and by-products such as esters and ethers in the final product mixture can be readily removed, as by distillation, for recycling, and the net yield of product is substantially exclusively the desired carboxylic acid. In the case of liquid-phase reaction, which is preferred, the organic compounds are easily separated from the metal-containing components, as by distillation. The reaction is suitably carried out in a reaction zone to which the carbon monoxide, the alcohol, the iodide, the co-catalyst and the promoter are fed.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but, as previously mentioned, it is a feature of the invention that excessively high pressures, which require special high-pressure equipment, are not necessary. In general, the reaction is effectively carried out by employing a carbon monoxide partial pressure which is preferably at least 15 but less than 2,000 psi, most preferably 15 to 1,000 psi and particularly 30 to 200 psi, although CO partial pressures of 1 to 5,000 or even up to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that rendered to maintain the liquid phase and in this case the reaction can be advantageously carried out in an autoclave or similar apparatus. The final reaction mixture will normally contain volatile components such as hydrocarbyl iodide, unreacted alcohol and may contain the corresponding ester and/or ether along with the product acid and these volatile components, after separation from the acid, can be recycled to the reaction. At the end of the desired residence time the reaction mixture is separated into its several constituents, as by distillation. Preferably, the reaction product is introduced into a distillation zone which may be a fractional distillation column, or a series of columns, effective to separate the volatile components from the product acid and to separate the product acid from the less volatile catalyst and promoter components of the reaction mixture. The boiling points of the volatile components are sufficiently far apart that their separation by conventional distillation presents no particular problem. Likewise, the higher-boiling organic components can be readily distilled away from the metal catalyst components and any organic promoter which may be in the form of a relatively non-volatile complex. The thus recovered co-catalyst as well as promoter, including the iodide component, can then be combined with fresh amounts of alcohol and carbon monoxide and reacted to produce additional quantities of carboxylic acid.

Although not necessary, the process can be carried out in the presence of a solvent or diluent. When the alcohol has a relatively low boiling point, as in the case of methanol, the presence of a higher-boiling solvent or diluent, preferably the product acid itself, e.g., acetic acid in the case of methanol, or the corresponding ester, e.g., methyl acetate, again in the case of methanol, will make it possible to employ more moderate total pressures. Alternatively, the solvent or diluent may be any organic solvent which is inert in the environment of the process such as hydrocarbons, e.g., octane, benzene, toluene, xylene and tetralin, or halogenated hycrocarbons such as the chlorobenzenes, e.g., trichlorobenzene, or carboxylic acids, or esters such as cellosolve acetate, and the like. Mixtures of solvents can also be used, such as mixtures of methyl acetate and acetic acid. The carboxylic acid, when used, should preferably correspond to the acid being produced since, as indicated above, the preferred solvent is one that is indigenous to the system, e.g., acetic acid and/or methyl acetate in the case of methanol carbonylation. A solvent or diluent, when not the product itself, is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The presence of minor amounts of water such as may be found in the commercial forms of the reactants is, however, entirely acceptable. Hydrogen which may be present as an impurity is not objectionable and even may tend to stabilize the catalyst. Indeed, in order to obtain low CO partial pressures the CO fed may be diluted with hydrogen or any inert gas such as those mentioned above. It has been surprisingly found that the presence of hydrogen does not lead to the formation of reduction products. The diluent gas, e.g., hydrogen, may generally be used in amount up to about 95%, if desired.

The co-catalyst components can be employed in any convenient form, viz., in the zero valent state or in any higher valent form. For example, the nickel and the molybdenum or tungsten can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide) phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Included among the catalyst components listed above are complexes of the metal co-catalyst components with organic promoter ligands derived from the organic promoters hereinafter described.

Particularly preferred are the elemental forms, compounds which are halides, especially iodides, and organic salts, e.g., salts of the monocarboxylic acid corresponding to the acid being produced. It will be understood that the foregoing compounds and complexes are merely illustrative of suitable forms of the several co-catalyst components and are not intended to be limiting.

The specified co-catalyst components employed may contain impurities normally associated with the commerciallly available metal or metal compounds and need not be purified further.

The organo-phosphorus promoter is preferably a phosphine, e.g. of the formula

wherein $R^1$, $R^2$ and $R^3$ may be the same or different, and are alkyl, cycloalkyl, aryl groups, amide groups, e.g., hexamethyl phosphorus triamide, or halogen atoms, preferably containing 1 to 20 carbon atoms in the case of alkyl and cycloalkyl groups and 6 to 18 carbon atoms in the case of aryl groups. Typical hydrocarbyl phosphines include trimethylphosphine, tripropylphosphine, tricyclohexylphosphine and triphenylphosphine. Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, N,N-diethyltoluamide, and imidazole.

Although generally the organic promoter is added separately to the catalyst system, it is also possible to add it as a complex with any of the co-catalyst metals, such as bis(triphenylphosphine) nickel dicarbonyl and tetrakis (triphenyl phosphite) nickel. Both free organic promoters and complexed promoters can also be used. When a complex of the organic promoter and the co-catalyst metal is used, free organic promoter can also be added.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 mol per 10 to 10,000 mols of alcohol, preferably 1 mol per 100 to 5,000 mols of alcohol and most preferably 1 mol per 500 to 1,000 mols of alcohol.

The ratio of nickel to the second co-catalyst component can vary. Typically, it is one mol of the nickel per 0.01 to 100 mols of the second co-catalyst component, preferably the nickel component is used in the amount of 1 mol per 0.1 to 20 mols, most preferably 1 mol per 1 to 10 mols of the second co-catalyst component.

The quantity of organic promoter can also vary widely but typically it is used in the amount of 1 mol per 0.1 to 10 mols of the co-catalyst components, preferably 1 mol per 0.5 to 5 mols, most preferably 1 mol per 1 to 5 mols of the co-catalyst component.

The amount of iodide component may also vary widely but, in general, it should be present in an amount of at least 10 mols (expressed as I) per hundred mols of alcohol. Typically, there are used 10 to 50 mols of the iodide per 100 mols of alcohol, preferably 17 to 35 mols per 100 mols. Ordinarily, more than 200 mols of iodide per 100 mols of alcohol are not used. It will be understood, however, that the iodide component does not have to be added to the system as a hydrocarbyl iodide but may be supplied as another organic iodide or as the hydroiodide or other inorganic iodide, e.g., a salt, such as the alkali metal or other metal salt, or even as elemental iodine.

As previously mentioned, the catalyst system of this invention comprises an organic promoter component, an iodide component and a molybdenum-nickel or tungsten-nickel co-catalyst component. The catalyst system of this invention permits the production of carboxylic acids in high yields in short reaction times without the use of Group VIII noble metals and the presence of the molybdenum or tungsten makes possible good results with relatively small amounts of co-catalyst component and reduced quantities of nickel in comparison with prior art processes involving a nickel-containing catalyst.

A particular embodiment of the catalyst comprising the molybdenum-nickel or tungsten-nickel co-catalyst component, the organic promoter component and the iodide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is an iodide source which is hydrogen iodide, iodine, an alkyl iodide wherein the alkyl group contains 1 to 20 carbon atoms or an alkali metal iodide, and Q is an organo-phosphorus compound or an organo-nitrogen compound wherein the phosphorus and the nitrogen are trivalent. Preferred are the nitrogen and phosphorus compounds previously indicated as being preferably used and in the most preferred form Q is a phosphine of the formula

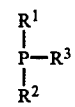

as hereinbefore defined, especially hydrocarbyl phosphines, the molar ratio of X to T being 0.1–10:1, the molar ratio of X+T to Q being 0 05–20:1 and the molar ratio of Z to X+T being 1–1,000:1.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of carboxylic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most perferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts are by weight and percentages are on a molar basis, unless otherwise indicated.

EXAMPLE 1

In this example, a magnetically-stirred Hastelloy Parr bomb with a glass liner is employed as the reaction vessel. The bomb is charged with methanol (150 parts), methyl iodide (350 parts), bis-triphenylphosphine nickel dicarbonyl (3.3 parts) plus molybdenum hexacarbonyl (3.3 parts) as co-catalyst, and triphenyl phosphine (3 parts), is swept out with argon and is pressured to 300 psig with carbon monoxide. The vessel is heated to 190° C. with stirring. At this point, the pressure is about 1,000 psig. Then the vessel is charged with 200 psig hydrogen to bring the pressure to 1,200 psig. The pressure is maintained at 1,200 psig by recharging carbon monoxide when needed. The temperature is maintained at 190° C. After 6 hours reaction time, G. C. analysis of the reaction effluent shows it to contain 11 mol % methyl acetate and 76 mol % acetic acid. This represents an 87% conversion of methanol to the acetyl group.

EXAMPLE 2

In this example, a magnetically-stirred Hastelloy Parr bomb with a glass liner is also employed as the reaction vessel. The bomb is charged with methanol (150 parts), methyl iodide (350 parts), nickel carbonyl (0.9 part) plus molybdenum hexacarbonyl (2 parts) as co-catalyst, and triphenylphosphine (6 parts), is swept out with argon and is pressured to 300 psig with carbon monoxide. The vessel is heated to 190° C. with stirring. At this point, the pressure is about 1,000 psig. Then the vessel is charged with additional 200 psig hydrogen to bring the pressure to 1,200 psig. The pressure is maintained at 1,200 psig by recharging carbon monoxide when needed. The temperature is maintained at 190° C. After 5 hours reaction time, G. C. analysis of the reaction effluent shows it to contain 10 mol % methyl acetate and 74 mol % acetic acid. This represents an 84% conversion of methanol to the acetyl group.

EXAMPLE 3

Using a reaction vessel as described in Examples 1 and 2, the bomb is charged with methanol (150 parts), methyl iodide (350 parts), nickel acetate (0.85 part) plus molybdenum hexacarbonyl (3.3 parts) as co-catalyst, and triphenylphosphine (6 parts), is swept out with argon and is pressured to 300 psig with carbon monoxide. The vessel is heated to 190° C. with stirring. Then the vessel is charged with an additional 200 psig hydrogen at which time the total pressure is 1,200 psig. The pressure is maintained at this value by recharging carbon monoxide when needed, and the temperature is maintained at 190° C. After 7 hours reaction time, G. C. analysis of the reaction effluent shows it to contain 8 mol % methyl acetate and 81 mol % acetic acid. This represents an 89% conversion of methanol to the acetyl group.

EXAMPLE 4

Again using a reaction vessel as defined in Examples 1 and 2, the bomb is charged with methanol (17.5 parts), methyl iodide (50 parts), bis-triphenylphosphine nickel dicarbonyl (1.0 part) plus molybdenum hexacarbonyl (1.5 parts) as cocatalyst, and triphenylphosphine (1.5 parts), is swept out with argon and is pressured to 500 psig with carbon monoxide. The vessel is heated to 185° C. with stirring and the temperature is maintained at 185° C. After 2 hours reaction time, G. C. analysis of the reaction effluent shows it to contain 21 mol % methyl acetate and 56 mol % acetic acid. This represents a 77% conversion of methanol to the acetyl group.

EXAMPLE 5

Using a magnetically-stirred Hastelloy Parr bomb with a glass liner is employed as the reaction vessel. The bomb is charged with methanol (10 parts), methyl acetate (7.5 parts), methyl iodide (50 parts) bis-triphenylphosphine nickel dicarbonyl (1 part) plus molybdenum hexacarbonyl (1.5 parts) as cocatalyst, and triphenylphosphine (1.5 parts), is swept out with argon and is pressured to 500 psig with carbon monoxide. The vessel is heated to 185° C. with stirring and the temperature is maintained at 185° C. After 1 hour reaction time, G. C. analysis of the reaction effluent shows it to contain 5 mol % methyl acetate in excess of the charged amount and 87 mol % acetic acid. Ths represents a 92% conversion of methanol to the acetyl group.

EXAMPLE 6

Using a reaction vessel as described in Example 5, the bomb is charged with methanol (59 parts), water (43.2 parts), methyl acetate (176 parts), methyl iodide (338 parts), bistriphenylphosphine nickel dicarbonyl (3.3 parts) plus molybdenum hexacarbonyl (3.3 parts) as co-catalyst, and triphenylphosphine (10 parts), is swept out with argon and is pressured to 300 psig with carbon monoxide. The vessel is heated to 190° C. with stirring at which time the pressure is about 1,000 psig. Then the vessel is charged with 200 psig hydrogen and the total pressure becomes 1,200 psig, and this pressure is maintained by recharging carbon monoxide when needed. The temperature is maintained at 190° C. After 4.5 hours reaction time, G. C. analysis of the reaction effluent shows it to contain 4 mol % methyl acetate and 85.4 mol % acetic acid. This represents an 89% conversion of methyl acetate and water to acetic acid in addition to a total conversion of methanol to acetic acid.

EXAMPLE 7

Using a reaction vessel as described in Example 5, the bomb is charged with water (43 parts), methyl acetate (175 parts), methyl iodide (353 parts), bis-triphenylphosphine nickel dicarbonyl (3.3 parts) plus molybdenum hexacarbonyl (3.3 parts) as co-catalyst, is swept out with argon and is pressured to 300 psig with carbon monoxide. The vessel is heated to 190° C. with stirring and the pressure increases to about 1,000 psig. Then the vessel is charged with an additional 200 psig hydrogen and the pressure is maintained at 1,200 psig by recharging carbon monoxide when needed, while the temperature is maintained at 2.5 hours reaction time, G. C. analysis of the 190° C. After 2.5 hours reaction time, G. C. analysis of the reaction effluent shows it to contain the same amount of methyl acetate as charged and 75 mol % acetic acid. This represents a 75% conversion of the methyl group to acetic acid.

EXAMPLE 8

Example 1 was repeated except that the bis-triphenylphosphine nickel dicarbonyl was replaced with nickel acetate. After 6 hours reaction time, G. C. analysis of the reaction mixture shows it to contain 15 mol % methyl acetate and 69 mol % acetic acid. This represents 85% conversion of methanol to the acetyl group.

EXAMPLE 9

Example 1 was again repeated except that the bis-triphenylphosphine nickel dicarbonyl was replaced with nickel iodide. After 5 hours reaction time, G. C. analysis of the reaction mixture shows it to contain 8 mol % methyl acetate and 83 mol % acetic acid. This represents 92% conversion of methanol to the acetyl group.

EXAMPLE 10

Again Example 1 was repeated except that the molybdenum carbonyl was replaced with molybdenum acetate. After 5 hours reaction time, G. C. analysis of the reaction mixture shows it to contain 20 mol % methyl acetate and 48 mol % acetic acid. This represents 68% conversion of methanol to the acetyl group.

EXAMPLE 11

Example 2 is repeated except that triphenylphosphine is replaced by an equivalent quantity of imidazole. Analysis of the reaction mixture shows a 45% conversion to the acetyl group.

EXAMPLE 12

A pressure reactor as described in Example 5 is charged with 450 g. ethyl iodide, 150 g. ethanol, 25 g. triphenylphosphine, 10 g. bis-triphenylphosphine nickel dicarbonyl, 15 g. molybdenum hexacarbonyl. The reactor is pressured with 200 psig hydrogen and up to 800 psig with carbon monoxide. The reactor is then heated up to 180° C. with stirring. The pressure increases to 1,250 psig and is maintained at that pressure by recharging carbon monoxide when needed. After 2 hours reaction time, G. C. analysis of the reaction mixture shows that it contained 91 mol % propionic acid and 4 mol % ethyl propionate.

What is claimed is:

1. A process for the preparation of a carboxylic acid which comprises reacting a hydrocarbyl alcohol with carbon monoxide in the presence of a molybdenum-nickel cocatalyst in the presence of an iodide and in the presence as a promoter of an organo-phosphorus compound or an organo-nitrogen compound wherein the phosphorus and nitrogen are trivalent.

2. A process as defined in claim 1, wherein the promoter is a phosphine.

* * * * *